United States Patent [19]
Darilek et al.

[11] Patent Number: 5,065,019
[45] Date of Patent: Nov. 12, 1991

[54] METHOD FOR DETERMINING PETROLEUM SATURATION IN A SUBSURFACE

[75] Inventors: Glenn T. Darilek; Dewey B. Keeton, III, both of San Antonio, Tex.

[73] Assignee: Southwest Research Institute, San Antonio, Tex.

[21] Appl. No.: 520,087

[22] Filed: May 7, 1990

[51] Int. Cl.$^5$ .................. G01V 9/04; G01N 21/64; G01N 21/85
[52] U.S. Cl. ................... 250/301; 37/118 A; 250/253; 250/461.1
[58] Field of Search ............ 250/301, 253, 461.1; 37/118 A, DIG. 20, DIG. 19, DIG. 14

[56] References Cited
FOREIGN PATENT DOCUMENTS
2751738 5/1979 Fed. Rep. of Germany ...... 250/301
2078941 1/1982 United Kingdom ............... 250/301

OTHER PUBLICATIONS
R. H. Hill, Jr., "Laser-Induced Luminescence", *Technology Today*, (Jun., 1989) reprint.

*Primary Examiner*—Constantine Hannaher
*Attorney, Agent, or Firm*—Baker & Botts

[57] ABSTRACT

A device and method for determining the depth of contaminant of petroleum based products in a subsurface, such as after an oil spill. The device is implemented either as a manual probe or as attachment to excavating equipment. The device has an ultraviolet radiation source for irradiating waves into the subsurface, and a visible-light detector for receiving fluorescence, which is induced by the contaminant when the contaminant is exposed to the ultraviolet radiation.

19 Claims, 4 Drawing Sheets

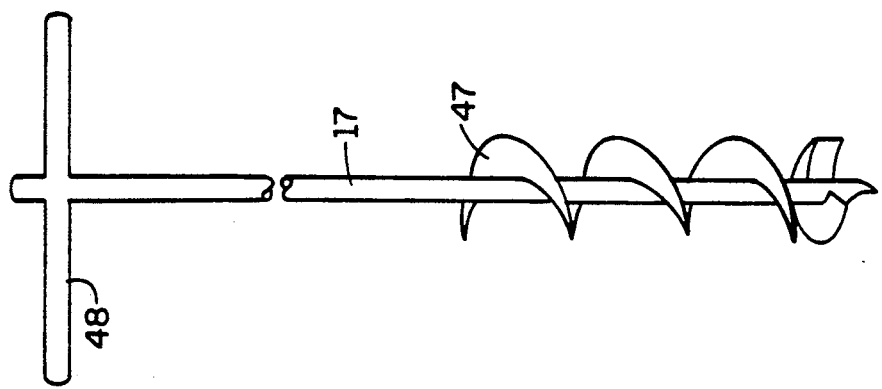
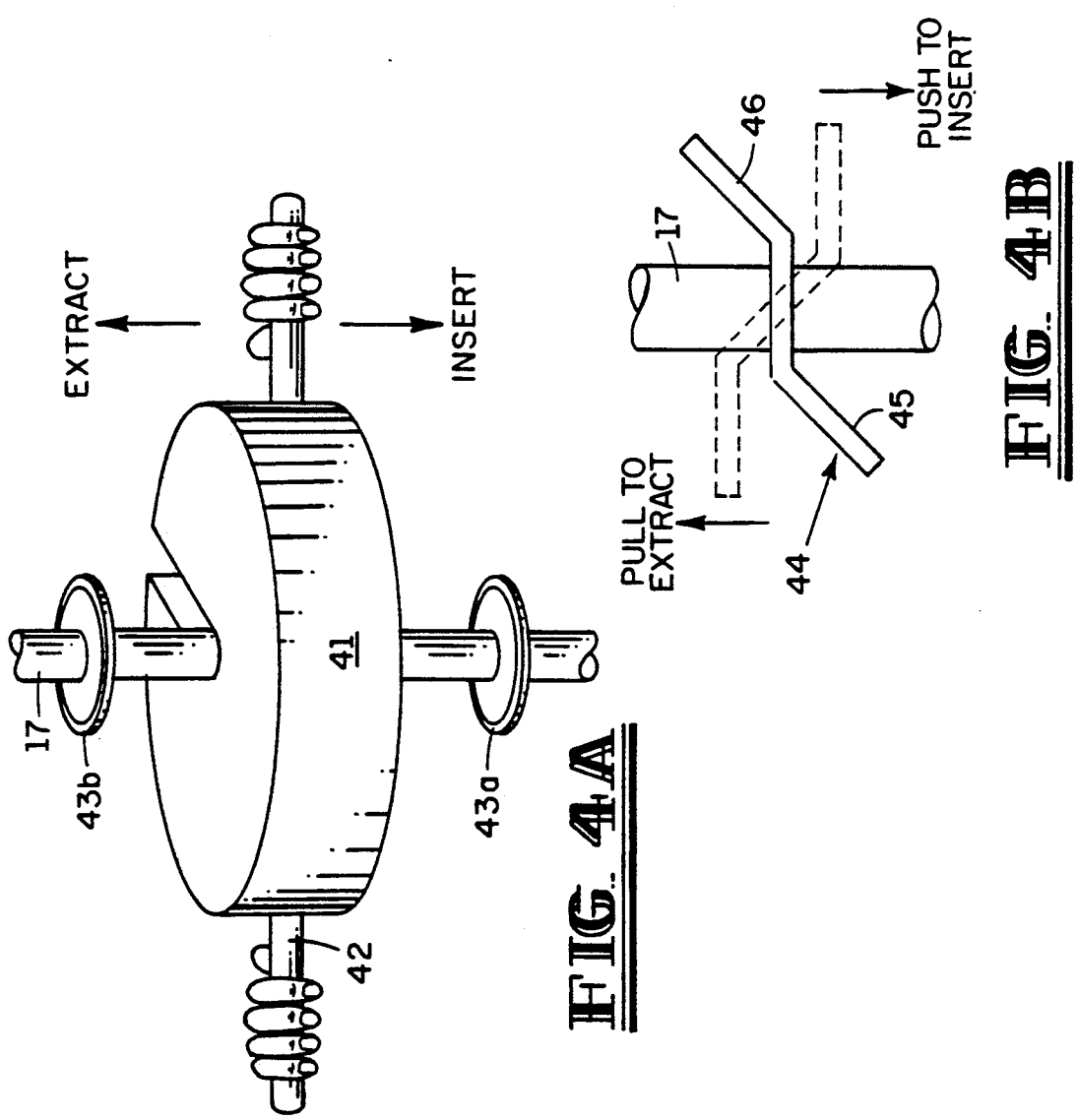

METHOD FOR DETERMINING PETROLEUM SATURATION IN A SUBSURFACE

TECHNICAL FIELD OF THE INVENTION

This invention relates to sensing and detecting devices and more particularly to a method for determining the depth of saturation of crude oil on a shoreline after an oil spill.

BACKGROUND OF THE INVENTION

Recent oil spills have focussed attention on the importance of efficient clean-up methods. Leaks in pipelines or oil-storage units or from oil tankers can cause surface and buried spills. Also, after a surface spill on a shoreline, wave action can result in burying the contaminated areas.

After an oil spill, clean-up operations are facilitated by first determining the location and depth of buried spills and the depth of surface spills. Once the location and depth of the spill is known, the resources and effort needed for clean-up operations can be allocated. For example, certain types of clean-up operations, such as microbial treatment, are more appropriate for shallower saturations than for deep ones.

One prior method for determining the depth of crude oil is the excavation of a test pit, which permits the saturation depth to be seen. However, this method is time consuming and requires expensive earth moving equipment at the site.

A second method is the use of electrical resistivity measurements. These methods measure the difference between the electrical resistivity of the contaminated and the uncontaminated areas. However, this method is prone to error, especially in the case of oil tanker spills. The oil in a sandy shoreline will displace air but not water, and because the shoreline is likely to be wet, the effect of the oil is small and difficult to measure.

A third method is ground penetrating radar measurements. A problem with this method is that the detectible difference between the contaminated and the uncontaminated areas is low. Thus, the contaminated area's interface does not produce a good reflector for electromagnetic waves.

A fourth method is seismic measurements. Problems with this method include lack of resolution and a poor reflecting interface. The attenuation of the seismic waves is high, especially in shorelines, which tend to consist of unconsolidated sand and gravel.

In light of the above problems with the prior art, a need exists for a reliable and accurate method for measuring the depth of crude oil in a subsurface.

SUMMARY OF THE INVENTION

One aspect of the invention is a device for determining the depth of petroleum-based contaminants in a subsurface. An ultraviolet radiation source irradiates the subsurface at specific depths. A visible light detector receives fluorescent light emitted by the contaminant in the subsurface when the contaminant is exposed to the ultraviolet radiation. The output of the detector is communicated to the user who may then relate the detected light to the depth of the contaminant.

A technical advantage of the invention is its reliability and versatility. It is not subject to the errors of other methods and provides good resolution of the interface between contaminated and clean soils. Furthermore, the method permits the detection of lower concentrations of petroleum-based contaminants than do other methods.

The device used to implement the invention is sufficiently portable for use in manual probes for reconnaissance type operations. The device can also be adapted for use in control systems for clean-up equipment, and is particularly useful as part of an automatic control system to control the depth at which the subsurface is removed.

BRIEF DESCRIPTION OF THE DRAWINGS

FIGS. 4A–4C illustrate various means for inserting and extracting the probe embodiment of the invention.

DETAILED DESCRIPTION OF THE INVENTION

General Implementation

A basic concept of the invention is the use of an ultraviolet-radiation source to illuminate the area under consideration, which causes heavy hydrocarbons to fluoresce. A visible-light detector is then used to detect this florescence. Although reference is made herein to "crude oil" and "oil spills", the invention is useful for locating any petroleum-based product.

Petroleum based products, such as crude oil, exhibit a pronounced florescence in response to long ultraviolet wavelengths. The emitted color of the light ranges from brown through green, gold, blue, and yellow, to white. Generally, heavier oils have more intense fluorescence. Although some minerals also fluoresce when subjected to ultraviolet irradiation, these minerals are not expected to appear in abundance in the areas of application, i.e., shoreline sand and gravel. Furthermore, although some shells and marine biota fluoresce under ultraviolet irradiation, it is believed that this fluorescence can be differentiated from that of oil. Either the level of fluorescence is expected to be substantially lower than that of the crude oil, or may be filtered on the basis of induced-fluorescence wavelengths.

Figure 1:
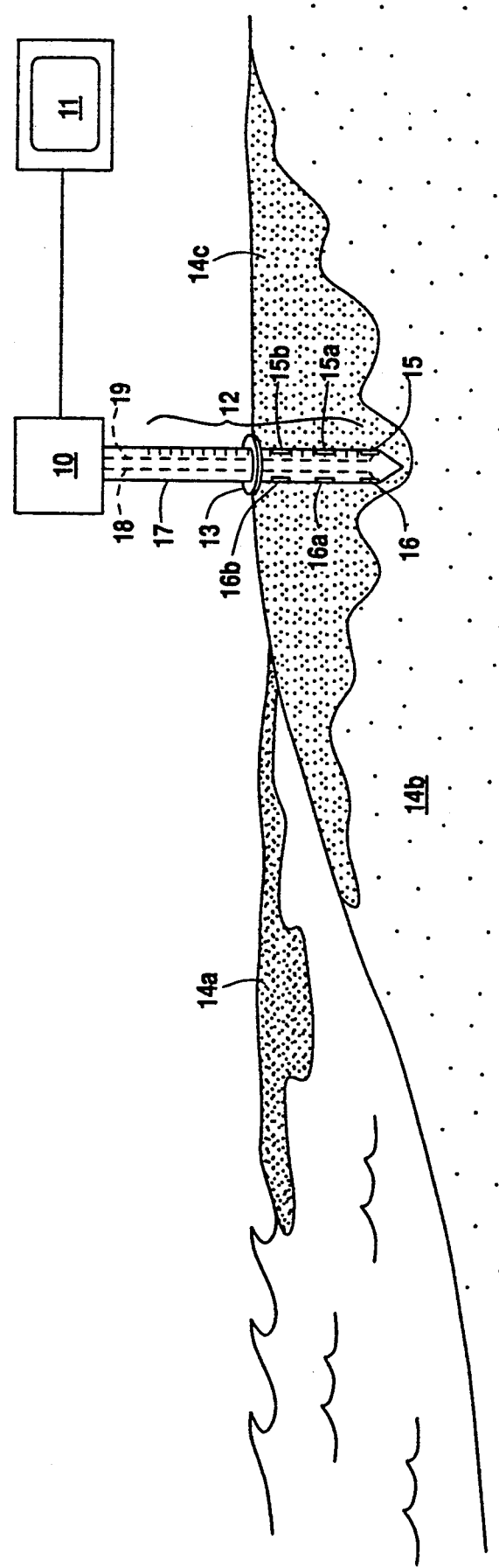
FIG. 1 is a perspective view of a shoreline that has be subjected to an oil spill, and also shows an enlarged view of a probe used to implement the invention.

FIG. 1 is a cut-away view of a shoreline which has been subjected to an oil spill 14a. The sand 14b comprising the shore line has been saturated at various depths with crude oil 14c. Although for convenience, the following description refers to sand as being the shoreline composition, the invention is equally useful with other shoreline compositions, such as gravel or soil, or mixtures of sand, gravel and soil.

FIG. 1 also illustrates, in block diagram form and greatly enlarged, the sensor 10 to which the invention is directed. As will be explained below, FIG. 1 illustrates sensor 10 implemented as a part of a probe 17, which is one application of sensor 10.

Figure 2:
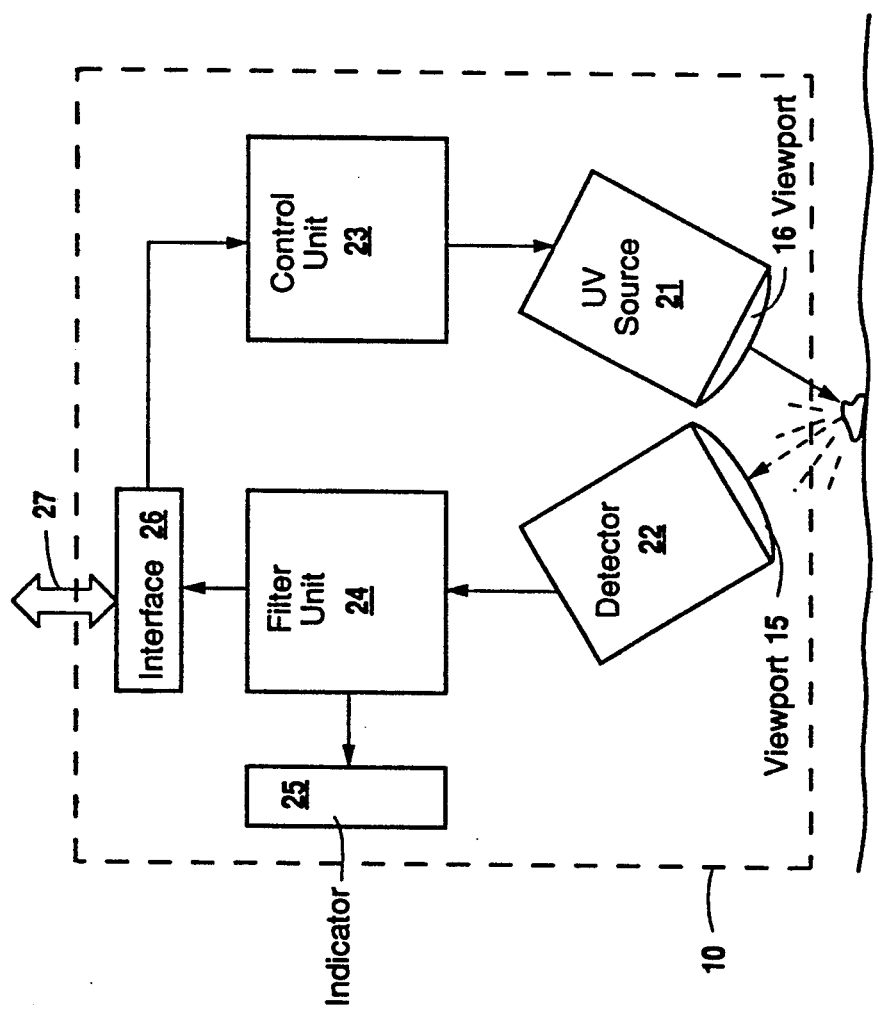
FIG. 2 is a block diagram of the petroleum sensing device that is the subject of the invention.

FIG. 2 is a block diagram of the internal components of sensor 10. Sensor 10 has several basic elements: ultraviolet source 21, visible-light detector 22, control unit 23, filter unit 24, indicator 25, and data communications interface 26.

Ultraviolet source 21 generates ultraviolet waves. Examples of ultraviolet source 21 are ultraviolet fluorescent tubes, phosphor-coated low pressure mercury lamps, and deuterium lamps. The wavelengths produced by ultraviolet source 21 are in a range of 300 to 400 nanometers, and are optimally in a band centered around 360 nanometers.

Examples of visible-light detector 22 are photodiodes and phototransistors. As explained above, petroleum products of different types and viscosities emit different wavelengths. Thus, visible-light detector 22 may be equipped with appropriate filters so that the presence of a petroleum products having known properties can be more easily detected. Filter unit 24 provides this function, as well as other filtering functions explained below.

Both ultraviolet source 21 and visible-light detector 22 are placed at angles with respect to each other. The illumination angle and the interception angle are selected for best detection of the desired diffuse emittance and rejection of specular reflections and ambient light. The need to eliminate ambient light depends on the application, with ambient light being a particular concern when the interface between sensor 10 and the soil permits it to interfere with induced-fluorescence detected by visible-light detector 22.

As indicated in FIG. 1, viewports 15 and 16 of ultraviolet source 21 and visible-light detector 22, respectively, are not necessary physically close to ultraviolet source 21 and visible-light detector 22. The configuration in this respect depends on the application. For example, when sensor 10 is used with a probe 17, such as in FIG. 1, it may be advantageous to separate viewports 15 and 16 from the rest of sensor 10 components. However, in other applications, where sensor 10 is best implemented as a compact and rugged unit, viewports 15 and 16 may be integral parts of ultraviolet source 21 and visible-light detector 22. This latter type of application is discussed below in connection with automatic control systems for excavation equipment.

Control unit 23 may be used to control ultraviolet source 21 so that it generates modulated light waves. As an example of this modulating ultraviolet embodiment, ultraviolet source 21 is switched on and off at a known frequency. The output of visible-light detector 22 is connected to filter 14, to discriminate against signals that are not of the modulating frequency. In this manner, induced fluorescence of the oil is measured and ambient light rejected. The modulation and filtering reduces ambient light interference, including noise caused by varying levels of light interference as sensor 10 is moved through sand. Variations in measured light intensity caused by rapid variations in the amount of ambient light can be similarly filtered.

Filter unit 24 may be any one of a number of known filtering devices, such as an electronic filter. More specifically, the filtering can be accomplished by means of narrow band synchronous or phase locked loop detection.

Indicator 25 is a means for providing output to the user of sensor 10 so that the user may immediately know whether a petroleum based substance is present in the subsurface. Any one of a number of indicators 25 could be used.

An advantage of the invention is that the output of visible-light detector 22 may be easily digitized and processed. This is particularly useful where sensor 10 is used in combination with a mapping scheme to plot the location of various depths of crude oil over a large area. Thus, referring to both FIGS. 1 and 2, a data processing unit 11 may be put in communication with sensor 10 via a data communications interface 26 and a bus 27. Furthermore, two-way communication between sensor 10 and data processing unit 17 could also be established whereby data processing unit 11 is used to control ultraviolet source or light detection parameters of sensor 10.

As shown in FIG. 1, if desired, viewports 15 and 16 may be kept free of accumulations of sand and oil by using fiber optics light bundles 18 and 19 to couple the active sensing elements, i.e., ultraviolet source 21 and visible-light detector 22, to the rest of sensor 10. Alternatively as shown in FIG. 3 to, or in combination with, fiber optics light bundles 18 and 19, viewports 15 and 16 could be imbedded in recesses and a compressed air stream or periodic flushing with detergent water used to keep them clear using a rinsing means 34.

Figure 3:
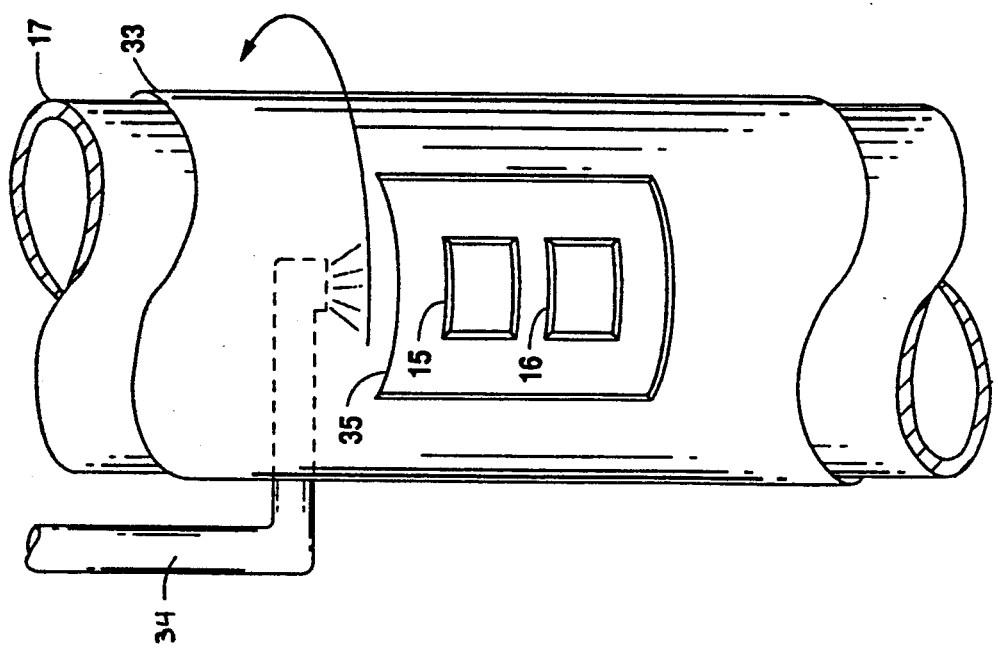
FIG. 3 represents the sensing device of FIG. 2, having a protective shield for the sensor viewports.

As shown in FIG. 3, a third means for providing clear viewports 15 and 16 is to house them in a concentric protective shield 33. When sensor 10 is in place and ready for operation, viewports 15 and 16 may be rotated to align with a window 35 in shield 33.

Sensor 10 is easily adapted for use with a number of applications, including a portable probe or as part of an automated control system for excavation equipment. The portable probe may be hand held or installed on mobile equipment. These applications are discussed in the following sections.

Portable Probe

In a number of applications, sensor 10 can be used as a portable probe for reconnaissance type measurements. FIG. 1 illustrates one such application, in which viewports 15 and 16 of sensor 10 are mounted at the end of a thin probe 17. If the spill is visible from the surface, the depth of oil penetration is determined by inserting probe 17 into the subsurface until sensor 10 indicates a lack of florescence.

A depth indicating means, such as indicator marks 12, on probe 17, is used to determine the depth of the oil, relative to the surface. By taking various measurements, the depth of a surface spill can be determined. Also, even if there is no visible oil on the surface, sensor 10 can be used to locate buried portions of the spill.

FIG. 1 illustrates an alternative to taking multiple depth readings, which is to provide multiple viewports 15 and 16, spaced at fixed intervals on probe 17. The output of these multiple viewports 15 and 16 can be processed by data processing system 11 to determine the depth of the oil.

Referring again to FIG. 1, to prevent ambient light from entering the sensitive area of sensor 10 via the entry point of probe 17 into the subsurface, a light shield 13 can be used. Light shield 13 is any attachment, such as a collar around probe 17, that blocks the light path down the hole caused by inserting probe 17.

FIGS. 4A-4C illustrate various means for manual insertion and extraction of probe 17 into and from the subsurface. The insertion and extraction means of FIG. 4A uses a sliding hammer 41 equipped with handle 42. Insertion of probe 17 is accomplished by propelling hammer 41 downward against lower restraint collar 43a. Extraction is accomplished by propelling hammer 41 upward against upper restraint collar 43b.

The insertion and extraction means of FIG. 4B uses a slip handle 44. By holding slip handle 44 with its center section perpendicular to probe 17, it can be adjusted up or down the length of probe 17 to a comfortable working height. Once slip handle 44 is positioned, pushing downward on lower bar 45 inserts probe 17 and pushing upward extracts probe 17.

The insertion and extraction means of FIG. 4C uses an auger 46 affixed to probe 17. Probe 17 is inserted by twisting it in the appropriate direction and is extracted by twisting it in the other direction. This embodiment of probe 17 may also be easily adapted for use with mechanical equipment as an alternative to manual operation.

Figure 5:
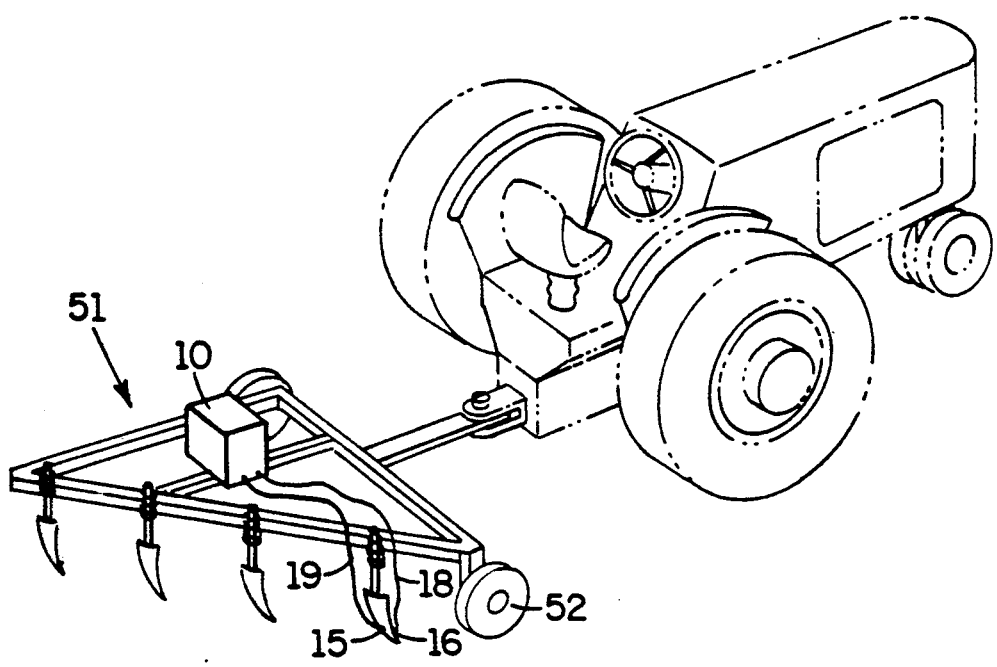
FIG. 5 illustrates the sensor of FIG. 2 mounted on a plow attachment.

FIG. 5 illustrates another portable probe device, in which, in lieu of probe 17, viewports 15 and 16 are mounted on a plow type attachment 51, pulled by a tractor or similar equipment and drawn through the sand to obtain a continuous reading of the depth of the oil. More specifically, viewports 15 and 16 are placed on a plow type blade or wheel attached to the pulling equipment. For purposes of this description, such a blade or wheel is referred to as a "tine". The exact configuration of the blade or wheel is not important so long as it is adequate for being pulled through the subsurface at a desired depth. Preferably viewports 15 and 16 are attached at the trailing edge to minimize wear and fouling. A distance measuring wheel 52 can also be provided so that readings from sensor 10 can be collected and mapped with data processing system 11.

Automated Excavation System

Figure 6:
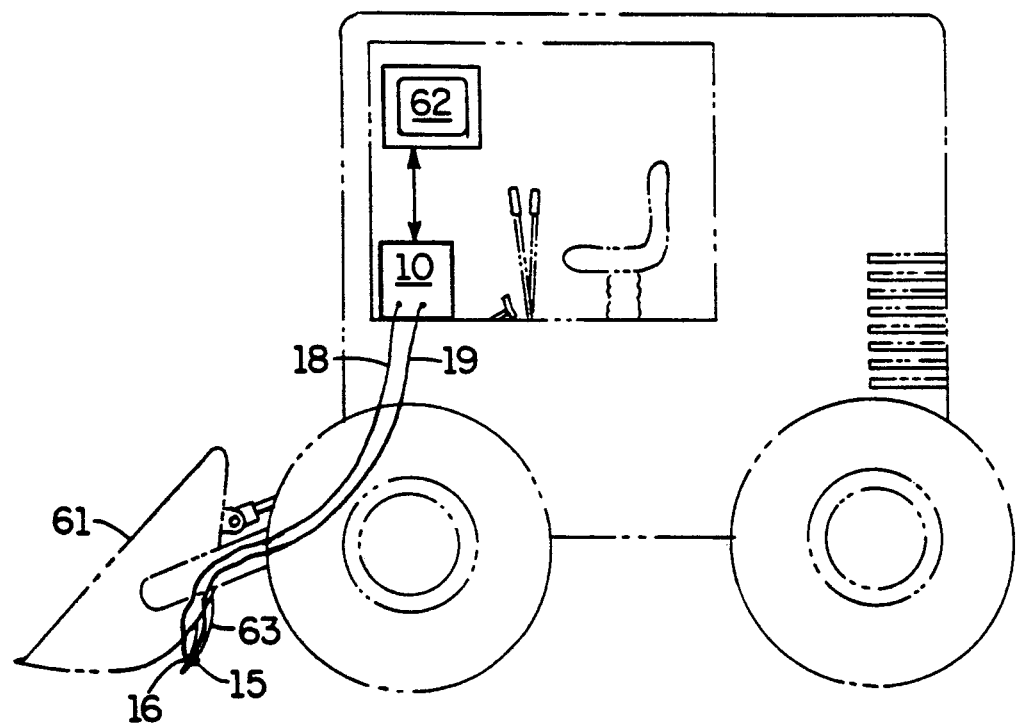
FIG. 6 illustrates the sensor of FIG. 2 used in connection with an automatic control system for excavation equipment.

FIG. 6 illustrates another embodiment of the invention, used in connection with a control system for a front end loader bucket or scraper, or similar attachments to excavation equipment. This application helps ensures that only contaminated sand is removed, and thus no more of the environment is disrupted than necessary.

The specific attachment illustrated in FIG. 6 is a loader bucket 61, to which viewports 15 and 16 are mounted. To mount sensor 10 to bucket 61 and to provide a path through the sand, sensor 10 can be mounted on a blade or wheel in front of the bucket 61.

The output of the sensor 10 is connected to an electronic control unit 62, which automatically controls the hydraulic circuit that raises and lowers bucket 61. If two or more sensors 10 are so mounted, they can be used to straddle the interface between contaminated sand and clean sand. The position of sensor 10 relative to bucket 61 may be made adjustable so that the amount of excavation below the interface can be set to any desired depth.

Other Embodiments

Although the invention has been described with reference to specific embodiments, this description is not meant to be construed in a limiting sense. Various modifications of the disclosed embodiments, as well as alternative embodiments will be apparent to persons skilled in the art. It is, therefore, contemplated that the appended claims will cover all modifications that fall within the true scope of the invention.

What is claimed is:

1. A device for determining the depth of a petroleum based substance in a granulated solid, comprising:
   an ultraviolet source for irradiating ultraviolet waves toward an inner surface of a granulated solid;
   a visible-light detector for receiving induced fluorescence of contaminant emitted from said inner surface when said contaminant is exposed to said ultraviolet radiation;
   wherein said source and said detector are placed at a predetermined angle with respect to each other to facilitate detection of diffuse emittance from said inner surface; and
   a filter attached to said detector to reduce interfering light detected by said detector.

2. The device of claim 1, wherein said filter is adapted to detect induced fluorescence of a contaminant having specific properties.

3. The device of claim 1, and further comprising a control unit for providing modulated ultraviolet radiation.

4. The device of claim 3, wherein said filter further detects induced fluorescence responsive to said modulated ultraviolet radiation.

5. The device of claim 3, and further comprising a demodulator for detecting induced fluorescence responsive to said modulated ultraviolet radiation.

6. The device of claim 1, and further comprising an indicator for displaying the output of said detector.

7. The device of claim 1, and further comprising a data communications interface for receiving the output of said detector and delivering said output to a data processing unit.

8. The device of claim 1, wherein said ultraviolet source is in communication with a viewport via optic fiber.

9. The device of claim 1, wherein said detector is in communication with a viewport via optic fiber.

10. A portable probe for determining the depth of a petroleum based substance in the subsurface of a granulated solid, comprising:
    a probe having an insertion end appropriate for insertion into the subsurface of a granulated solid and an operating end to be held by a user;
    an ultraviolet source for irradiating ultraviolet waves into said subsurface of a granulated solid, having a source viewport at the insertion end of said probe;
    a visible-light detector for receiving induced fluoroescence of said contaminant in said subsurface of a granulated solid when said contaminant is exposed to said ultraviolet radiation, having a detector viewport at the insertion end of said probe;
    wherein said source viewport and said detector viewport are placed at a predetermined angle with respect to each other, such that diffuse emittance from an inner surface adjacent to said probe is received by said detector viewport.

11. The probe of claim 10, and further comprising a rinsing means for keeping said ultraviolet source free of accumulations during use.

12. The probe of claim 10, and further comprising a protective shield for keeping said ultraviolet source free of accumulations during insertion of said probe into said solid, and having a window, such that said viewport of said detector may be moved after insertion to align with said opening.

13. The probe of claim 10, and further comprising a plurality of said visible-light detectors whose viewports are attached at varying depths on said probe.

14. An attachment for excavation equipment for use in determining the depth of a petroleum based contaminant in a subsurface, comprising:

a tine for attachment to excavation equipment and for moving through said subsurface at a desired depth;

an ultraviolet source for irradiating ultraviolet waves into the subsurface, having a viewport attached to said tine; and a visible-light detector for receiving induced fluorescence of contaminant in said subsurface when said contaminant is exposed to said ultraviolet radiation, having a viewport attached to said tine.

15. The attachment of claim 14, and further comprising a control system for receiving the output of said detector and controlling the depth at which excavation occurs.

16. A method for determining the depth of a petroleum based substance in a granulated solid, comprising the steps of:

inserting a sensor viewport and a detector viewport into said granulated solid;

introducing ultraviolet radiation into said subsurface via said sensor viewport at a predetermined incident angle with respect to the interface between said viewport and said granulated solid;

detecting induced fluorescence of said contaminant in response to said ultraviolet radiation via said detector viewport at an angle relative to said incident angle that facilitates reception of diffuse emittance; and relating the location of said detected fluorescence to the depth of said contaminant.

17. The method of claim 16, and further comprising the step of preforming said relating step with data processing equipment.

18. The method of claim 16, and further comprising the step of selecting said angle such that specular reflections are rejected.

19. The method of claim 16, and further comprising the step of selecting said angle such that ambient light is rejected.

* * * * *